United States Patent [19]
Agbodoe et al.

[11] Patent Number: 5,254,079
[45] Date of Patent: Oct. 19, 1993

[54] HEAD CLAMP

[75] Inventors: Victor B. Agbodoe, Boston; Edward L. Gallini, Marion; Robert E. David, Duxbury, all of Mass.

[73] Assignee: Codman & Shurtleff, Inc., Randolph, Mass.

[21] Appl. No.: 921,867

[22] Filed: Jul. 29, 1992

[51] Int. Cl.$^5$ .............................................. A61H 1/02
[52] U.S. Cl. .................................. 602/32; 602/36; 602/37
[58] Field of Search ............... 5/637; 606/130, 56, 606/96; 602/37, 32, 17; 128/75

[56] References Cited

U.S. PATENT DOCUMENTS

| | | | |
|---|---|---|---|
| 2,966,383 | 12/1960 | Boetcker et al. | 5/637 |
| 3,099,441 | 7/1963 | Ries | 269/328 |
| 3,401,688 | 9/1968 | Crutchfield | 602/37 |
| 3,835,861 | 9/1974 | Kees et al. | 128/346 |
| 3,923,046 | 12/1975 | Heifetz | 602/37 |
| 4,108,426 | 8/1978 | Lindstroem et al. | 5/637 |
| 4,169,478 | 10/1979 | Hickmann | 5/637 |
| 4,545,572 | 10/1985 | Day | 269/328 |
| 4,667,660 | 5/1987 | Eingorn | 602/37 |

*Primary Examiner*—Richard J. Apley
*Assistant Examiner*—Beverly A. Meindl
*Attorney, Agent, or Firm*—Michael Q. Tatlow

[57] ABSTRACT

A head clamp which includes a frame with two arms, a bracket on one of the arms capable of rotation to adjust the position of head engaging pins affixed at the ends of the arms. The bracket is rotatable but held in position by a plurality of index pins fixed in apertures in a plate and the bracket is capable of being rotated by moving the pins out of the apertures and rotating the bracket when the head engaging pins have been removed from the patient.

2 Claims, 4 Drawing Sheets

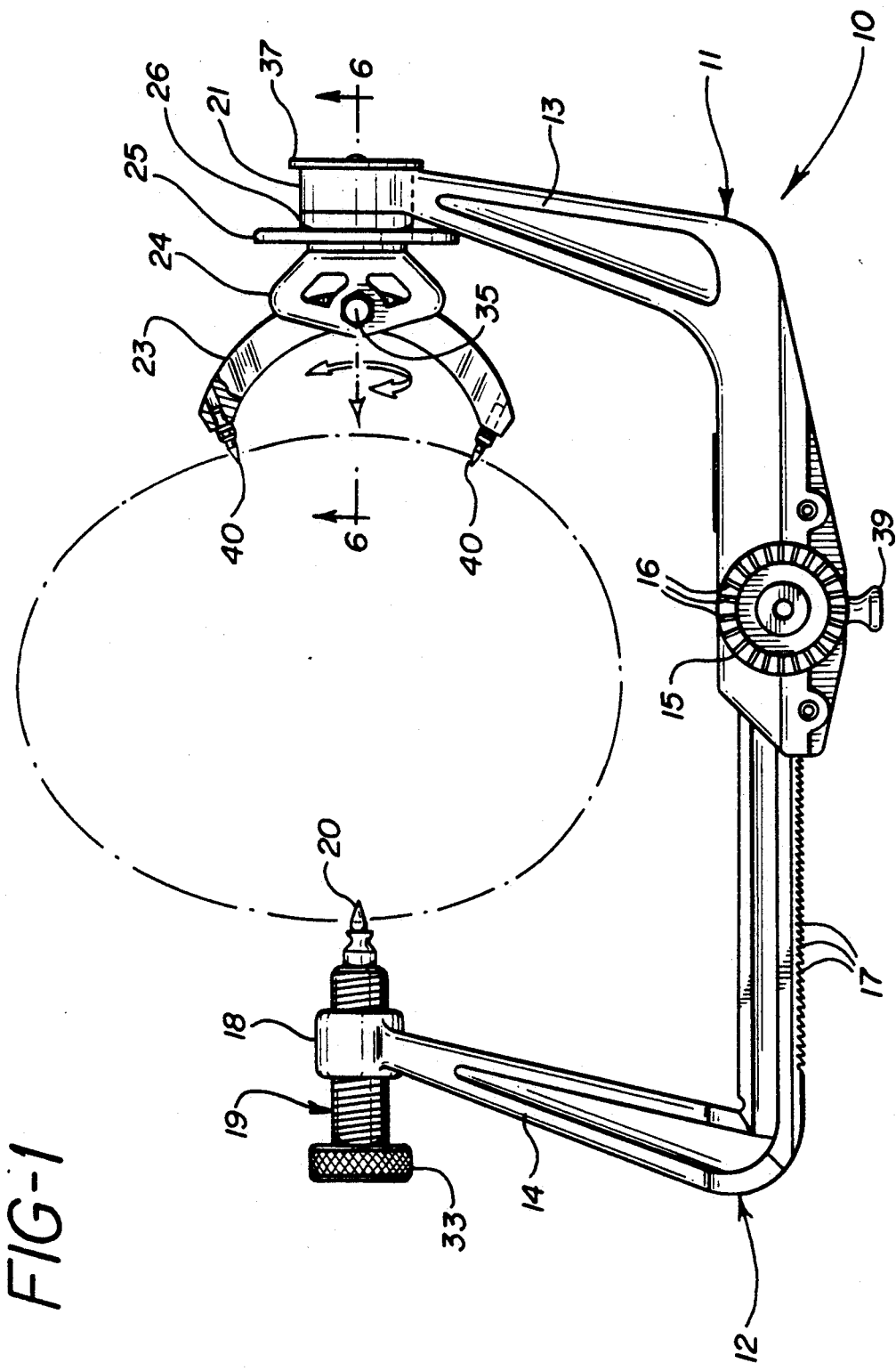

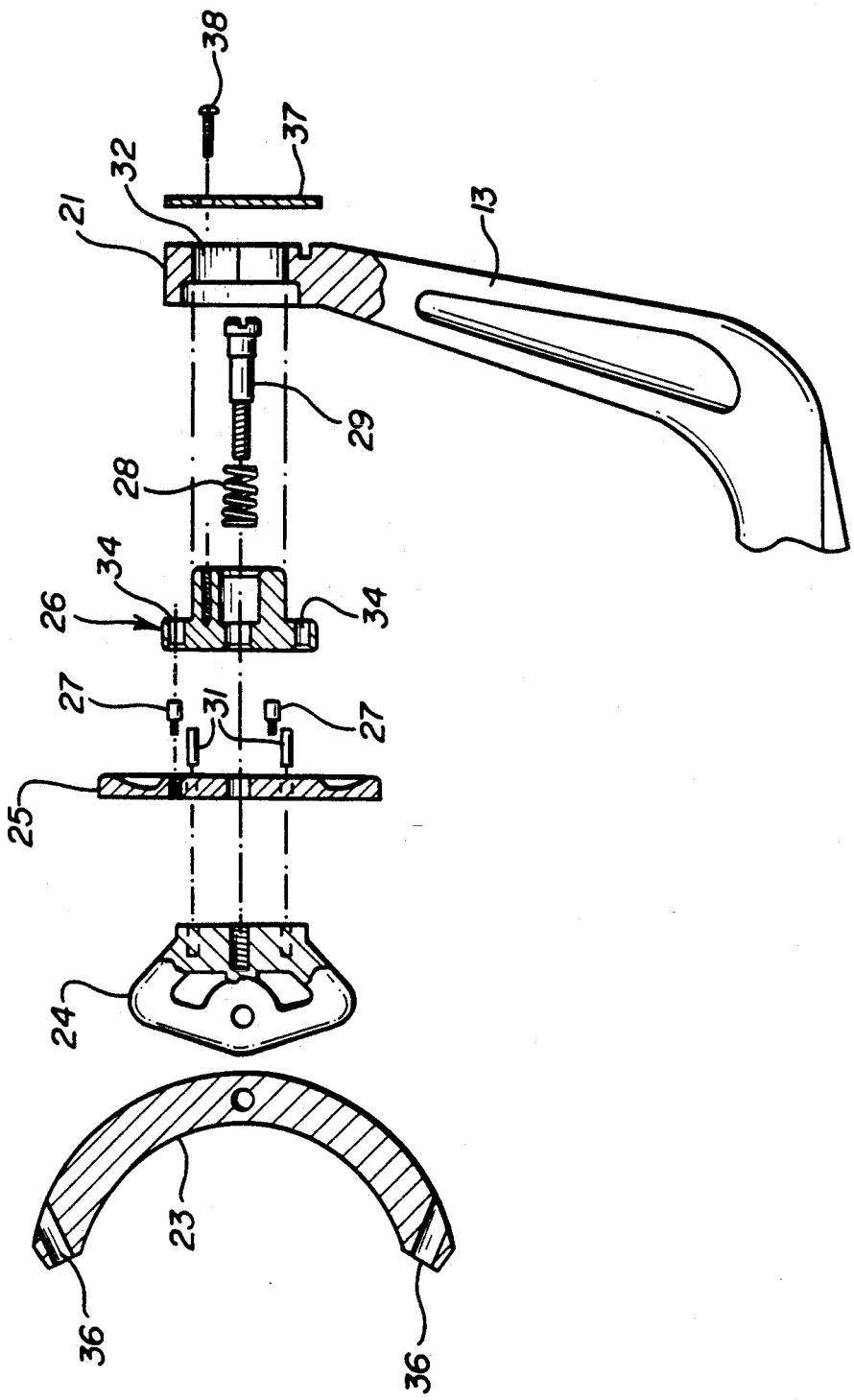

HEAD CLAMP

The present invention relates to a skull clamp or surgical head clamp to hold the head of the patient in position for neurosurgical operations and for other procedures involving the patients head.

BACKGROUND OF THE INVENTION

Surgical head clamps or skull clamps generally are provided with two types of mechanisms to hold the head in position. The first type of clamps use pads that are forced against the patient's head to hold the head in position. Examples of head clamps of type are disclosed in U.S. Pat. Nos. 4,108,426 and 4,545,572.

The second type of head clamps use a series of head engaging pins which engage the patient's skull at three points and provide positive anchorage of the head engaging pins into the skull. If the head engaging pins are held in a stable held in position, there is little likelihood that the skull will move relative to the head engaging pins during the surgical procedure.

The head clamp disclosed in U.S. Pat. No. 2,966,383 shows a three pin arrangement with the head engaging pins carried on hinged arms.

U.S. Pat. No. 3,099,441 discloses a surgical head clamp which contains two head engaging pins on a bracket supported by an arm and a third head engaging pin supported by another arm in the device. The two arms are brought together to adjust the space between the head engaging pins to fit the dimensions of the patient's head.

U.S. Pat. No. 3,835,861 discloses a surgical head clamp having three head engaging pins with two of the pins on a bracket and a third pin on a moveable pin carrier in which one of the pins is held on a threaded pin carrier so finer adjustments in the relationship of the head engaging pins to the patient can be made.

U.S. Pat. No. 4,169,478 also discloses a surgical head clamp with three head engaging pins which is similar to that shown in U.S. Pat. No. 3,835,861. The head clamp includes a mechanism to rotate the bracket containing the two pins and reposition the head of the patient without releasing the head engaging pins from the patient's skull. The mechanism employed to allow the rotation includes a number of ball actuators that are received in sockets. The rotation of an operating handle displaces the balls and allows the bracket to be rotated to permit the turning of the head without releasing the pin members from the head.

Although the surgical head clamp disclosed in U.S. Pat. No. 4,169,478 does offer certain advantages to the physicians, the problem exists in that the bracket can be inadvertently turned which may cause the head to move in the bracket and could cause injury to the patient. The weight of the patient in certain operating positions could exert a force against the bracket which might cause the bracket to turn if the ball actuators are not firmly seated in the sockets of the actuator disk.

BRIEF SUMMARY OF THE INVENTION

The head clamp of the present invention provides the flexibility of the devices described above but prevents the inadvertent rotation of the bracket. The present head clamp includes two head engaging pins secured to a rocker arm on a bracket and a third head engaging pin which is held in a movable pin carrier. When the present head clamp is in use, there are a number of index pins positioned in apertures in an index plate which positively lock the bracket rocker arm to prevent the inadvertent rotation of the rocker arm bracket and the head retaining pins. The use of the index pins in the present head clamp not only prevents rotation but also provide a more stable head clamp which can better withstand the forces that may be exerted on the clamp during the surgical procedure. The number of index pins and apertures are preferably selected so that the bracket can be rotated in increments of 20 degrees or less. In order to rotate the rocker arm bracket in the head clamp of the present invention, the head engaging pins must be removed from the patient's head. The bracket can be rotated to a new position by forcing the bracket inward toward the single pin on the moveable pin carrier. If the patient's head was still secured in the head clamp, this action would drive the pins in to the patient's skull and could cause injury to the patient. Therefore, the head engaging pins must be removed from the patient's head before the bracket is repositioned.

BRIEF DESCRIPTION OF THE DRAWINGS

In the drawings, FIG. 1 is a plan view of the surgical head clamp in the present invention showing the relative position of the head in dash lines.

FIG. 2 is an exploded view of the pin locking mechanism used in the present skull clamp.

DETAIL DESCRIPTION OF THE INVENTION

Figure 4:
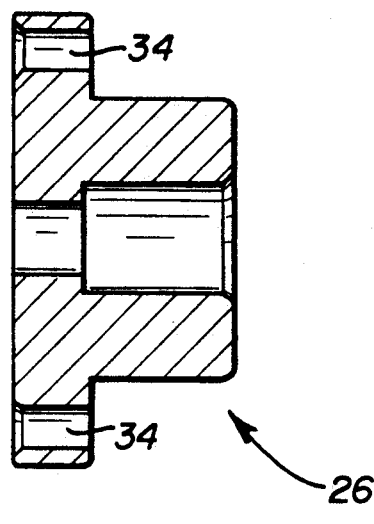
FIG. 4 is a cross sectional view along the lines 4—4 of FIG. 3.

The basic skull clamp of the present invention as shown in FIG. 1 is similar to the clamp which is shown in U.S. Pat. Nos. 3,835,861 and 4,169,478. The clamp 10 includes a main fixed section 11 and a ratchet section 12. These sections are connected in a telescoping relationship with the ratchet section 12 being capable of telescoping into the fixed section 11. The ratchet section 12 has a number of teeth 17 which can engage teeth (not shown) on a plunger lock 39 to lock the ratchet section the fixed section of the clamp. On fixed section 11 there is an arm 13 which terminates in a boss 21 which has a hexagonal interior configuration. An arm 14 on ratchet section 12 terminates in an internally threaded boss 18 to receive a pin carrier 19. The pin carrier 19 has a knob 33 at one end and a pin receiving bore at the other end. A head engaging pin 20 is seated in the bore.

The head clamp is secured to the operating room table through a sunburst clamp 15 which has teeth 16 to engage matching teeth on a support (not shown) which would be affixed to the operating room table.

Figure 3:
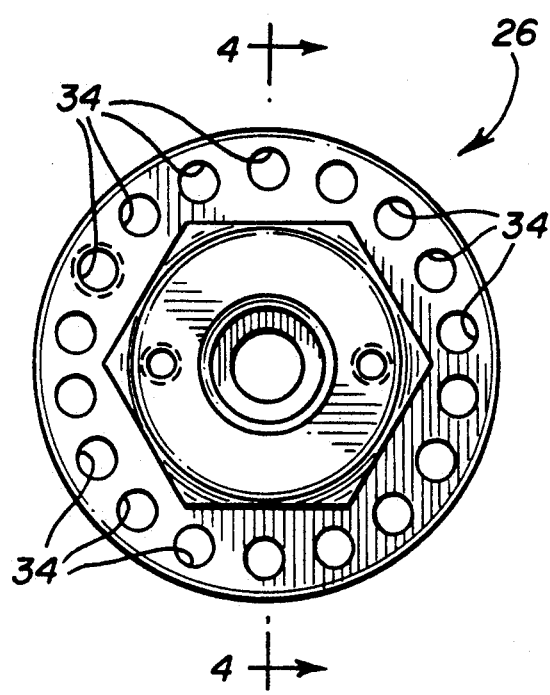
FIG. 3 is a plan view of the circular index plate used to retain the skull clamp in position.
Figure 5:
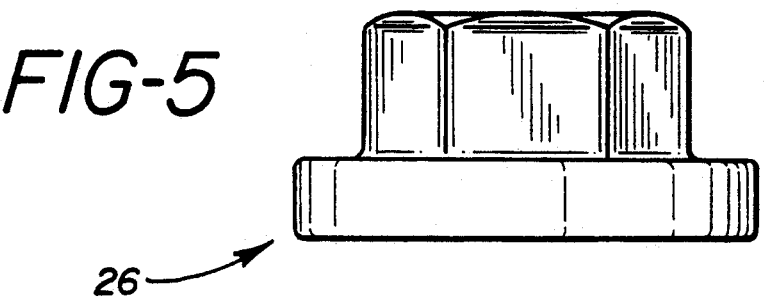
FIG. 5 is an side view of the retaining plate shown in FIG. 3 and FIG. 4.
Figure 6:
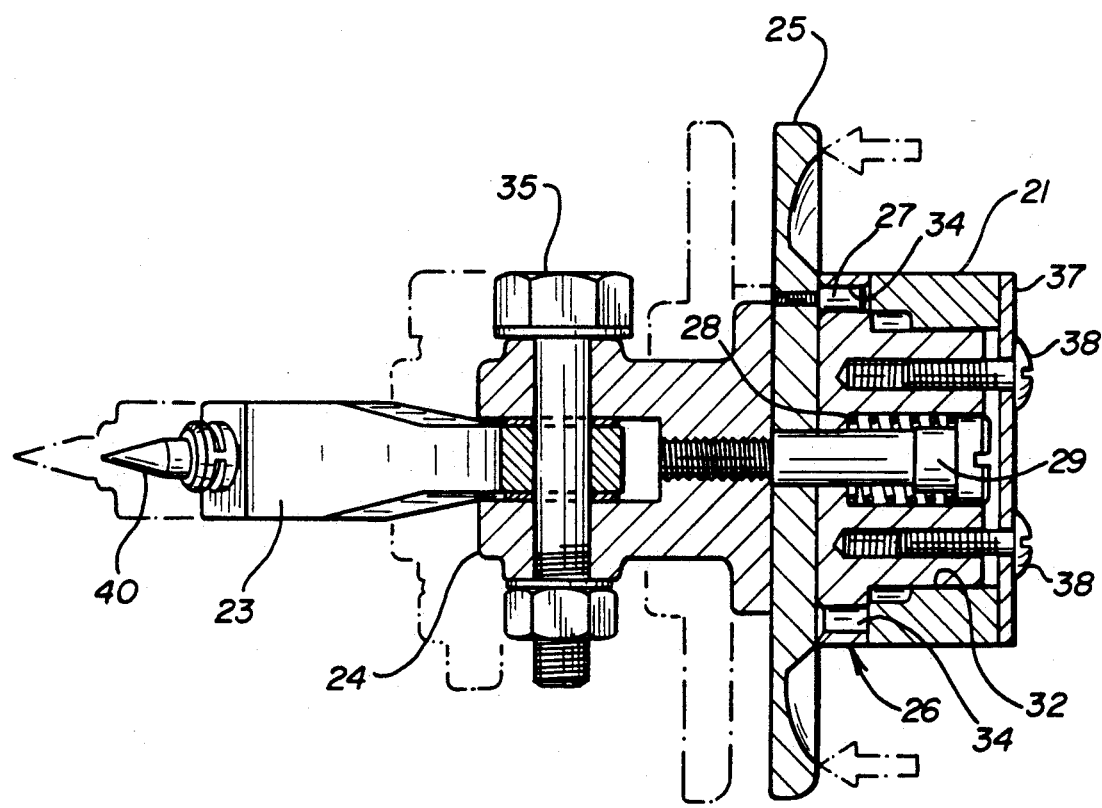
FIG. 6 is a detailed view, partially in cross section of the rocker arm and index plate of the present invention.

As shown in FIG. 2, the fixed arm 13, has a boss 21, into which is fitted an index plate 26. The index plate has a hexagonal shape which will fit into the hexagonal opening in the boss 21. Around the periphery of the index plate 26, there are a series of apertures 34, best shown in FIG. 3. There is an index pin retainer plate 25, which carries a series of at least two and preferably three index pins 27 secured into the plate. These index pins 27 are located on the index pin retainer plate so that they will align with the apertures 34, in the index plate.

There is a rocker arm bracket 24 affixed to the pin retainer plate. A rocker arm 23 is affixed to the bracket with a bolt 35. There are bores 36, in the ends of the rocker arm to receive the head engaging pins 40. The bracket 24 is affixed to the index pin retaining plate with interrolled pins and screws 31. The rocker arm 23 is affixed to the bracket 24 with a single bolt 35 (FIG. 1) to allow pivotal movement of the rocker arm around the axis of the bolt 35.

The alignment of the index pins on the index pin retainer plate is such that the index pins will align with apertures in the index plate to allow multiple positions where the index pins will register in the apertures. For example, if there are three equally spaced index pins on the index pin retainer plate, there should be a number of equally spaced apertures on the index plate which are divisible by three, the number of pins. If there are 18 apertures in the periphery of the index plate equally spaced, the apertures would be 20° apart. The bracket could therefore be adjusted at 20° increments of rotation. If there were four pins on the index pin retaining plate and twenty apertures on the index plate, the bracket could be adjusted at 18° increments.

There is a screw 29, which is fitted into and against a spring 28, and which extends through the index plate and the index pin retainer plate to secure the rocker arm bracket, the index pin retainer plate, and the index plate together. The spring 28 acts to bias the index pins 27, into the apertures in the index plate. Moving the bracket inwardly toward the pin 20 will compress the spring 28. The expansion of the spring will force the index pins 27 into the apertures 34. There is a cover 37, covering the screw 29 and the end of the index plate 26.

When the present skull clamp is used, the arms are separated and the patient's head is positioned between the arms. The arms are then moved together, until the head engaging skull pins are in contact with the patient's skull. The pin carrier 19 is then moved in toward the patient's skull which forces the head engaging pin 20 and the head engaging pins 40 into the bony portion of the skull a sufficient distance to hold the skull in the correct position for the surgical procedure. In the event that it is desired to reposition the patient's skull it is necessary to remove the pressure from the pin 20 in pin carrier 19 by rotating the pin carrier out of the internally threaded boss to remove the head engaging pins 20 from the patient's skull. During this time period the patient's head must be fully supported by other means. To reposition the pins, it is necessary to pull the rocker arm bracket 24 toward head engaging pin 20 a sufficient distance so that the index pins 27 are removed from the apertures 34 in the index plate 26. The bracket can be rotated and index pins 27 repositioned in different apertures 34 to lock the bracket into a different position.

We claim:

1. In a surgical head clamp including a frame, a first head engaging pin supported on the frame, a bracket rotatably supported on the frame aligned with and spaced from the first head engaging pin, second and third head engaging pins mounted on the bracket, means for advancing the first head engaging pin axially toward the bracket to cause the head engaging pins to engage the head, the first head engaging pin being aligned with the axis of rotation of the bracket, the improvement comprising means to positively lock said bracket to said frame to prevent accidental rotation of said bracket, including a retainer plate attached to said bracket, a plurality of index pins affixed at spaced apart locations to said retainer plate, an index plate affixed to said frame, said index plate having a plurality of apertures to receive the index pins, means to bias the retainer plate against the index plate to releasably secure the index pins in said apertures with a force to allow the axially and rotational movement of said retainer plate to reposition the index pins in the apertures to thereby reposition said bracket.

2. The head clamp of claim 1 in which the bracket can be rotated in increments of 20°.

* * * * *